US00PP21169P2

(12) United States Plant Patent
van der Jagt

(10) Patent No.: US PP21,169 P2
(45) Date of Patent: Jul. 20, 2010

(54) *HYDRANGEA* PLANT NAMED 'FANTASIA'

(50) Latin Name: *Hydrangea macrophylla*
Varietal Denomination: Fantasia

(76) Inventor: Wilhelmus G. van der Jagt, Herenweg 19, Leimuiden 2451 VP (NL)

( * ) Notice: Subject to any disclaimer, the term of this patent is extended or adjusted under 35 U.S.C. 154(b) by 0 days.

(21) Appl. No.: 12/454,904

(22) Filed: May 26, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

European Plant Breeder's Rights No. 19832 granted Apr. 16, 2007 http://www.cpvoextranet.cpvo.europa.eu.

*Primary Examiner*—Susan B McCormick Ewoldt
(74) *Attorney, Agent, or Firm*—Audrey Charles

(57) ABSTRACT

A new and distinct cultivar of *Hydrangea* plant named 'Fantasia', characterized by pink and green bicolored flowers, medium green-colored foliage, and moderately vigorous, broad-upright growth habit, is disclosed.

1 Drawing Sheet

Latin name of genus and species of plant claimed: *Hydrangea macrophylla.*

Variety denomination: 'Fantasia'.

BACKGROUND OF THE INVENTION

The present invention relates to a new and distinct cultivar of *Hydrangea* plant botanically known as *Hydrangea macrophylla* and hereinafter referred to by the cultivar name 'Fantasia'. 'Fantasia' is a deciduous shrub grown for landscape and potted plant use. The new cultivar originated in a controlled breeding program in Leimuiden, The Netherlands during 2000. The objective of the breeding program was the development of *Hydrangea* varieties with novel flower colors.

The new cultivar originated from a cross pollination. The female (seed) parent of the new cultivar is the *Hydrangea macrophylla* 'Adria', not patented, characterized by its pink-colored florets. The male (pollen) parent of the new cultivar is the proprietary *Hydrangea macrophylla* breeding selection designated 98-92-1, not patented, characterized by its pink-colored florets that mature to green, large leaves and long stem length. The new cultivar was discovered and selected as a single flowering plant within the progeny of the above stated cross-pollination during 2003 in a controlled environment at Leimuiden, The Netherlands.

Asexual reproduction of the new cultivar by softwood stem cuttings since 2003 at Leimuiden, The Netherlands has demonstrated that the new cultivar reproduces true to type with all of the characteristics, as herein described, firmly fixed and retained through successive generations of such asexual propagation.

SUMMARY OF THE INVENTION

The following are the most outstanding and distinguishing characteristics of this new cultivar when grown under normal horticultural practices in Leimuiden, The Netherlands:

1. Pink and green bicolored flowers;
2. Medium green-colored foliage; and
3. Moderately vigorous, broad-upright growth habit.

Plants of the new cultivar differ from plants of the female parent primarily in flower color and from plants of the male parent primarily in flower color, leaf size and stem length. 'Fantasia' has smaller leaves and shorter stems than the male parent.

Of the many commercially available *Hydrangea* cultivars, the most similar in comparison to the new cultivar is 'Masja', not patented. However, in comparison, plants of the new cultivar 'Fantasia' differ from plants of 'Masja' in at least the following characteristics:

1. Plants of the new cultivar have a flower color different from plants of 'Masja';
2. Plants of the new cultivar have moderately glossy leaves while leaves of 'Masja' are glossy; and
3. Plants of the new cultivar have smaller florets, as measured by floret diameter, than plants of 'Masja'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Fantasia'. The plants were grown for approximately 2 years in a 3-liter container in Leimuiden, The Netherlands in a greenhouse location.

DETAILED BOTANICAL DESCRIPTION

Figure 1:
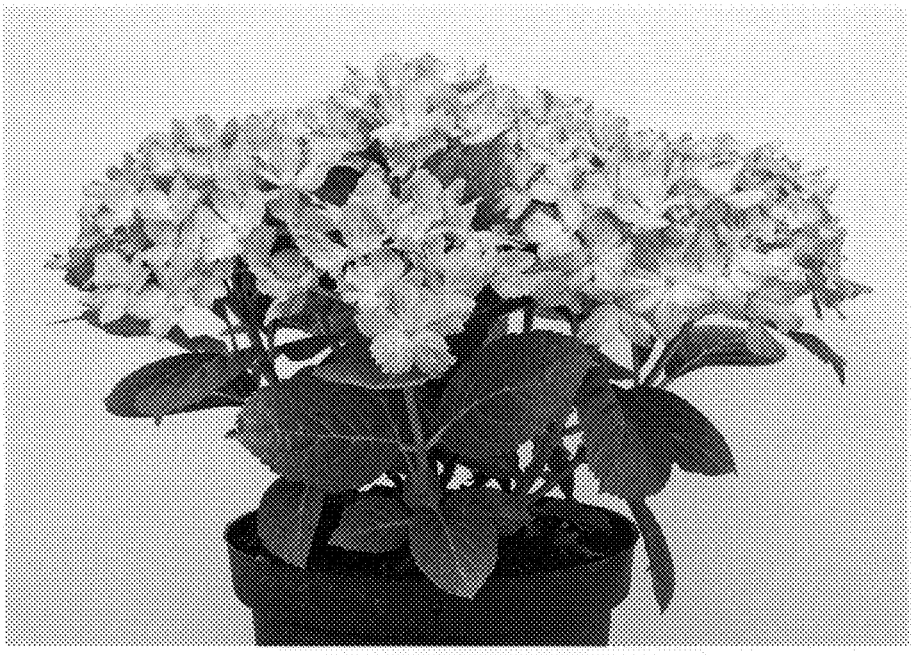
FIG. 1 illustrates a side view of the overall growth and flowering habit of 'Fantasia'.
Figure 2:
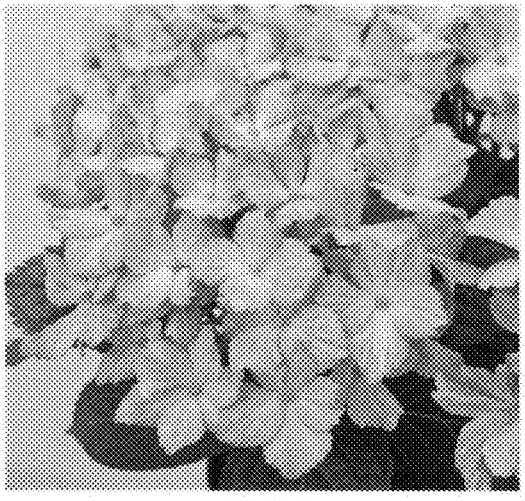
FIG. 2 illustrates a close-up view of an inflorescence of 'Fantasia'.
Figure 3:
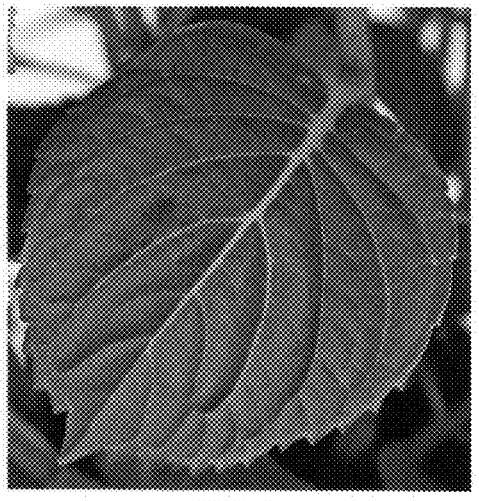
FIG. 3 illustrates a close-up view of a leaf of 'Fantasia'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The data which define these characteristics were collected from asexual reproductions carried out in Leimuiden, The Netherlands. The plant history was taken in September on 2-year-old plants which were planted and grown in 3-liter containers a greenhouse environment with daytime temperatures between 12° C. and 22° C. and nighttime temperatures between 8° C. and 18° C. No pinching, growth retardants or photoperiodic treatments were used. Observations were made when the plants were in natural daylight conditions.

Botanical classification: *Hydrangea macrophylla* cultivar 'Fantasia'.

Parentage:

*Female parent.*—*Hydrangea macrophylla* 'Adria', not patented.

*Male parent.*—Proprietary *Hydrangea macrophylla* breeding selection designated 98-92-1.

Propagation:

*Type cutting.*—Softwood stem.

*Time to initiate roots in summer.*—4 weeks with approximate temperatures of 20° C. day/18° C. night.

*Time to initiate roots in winter.*—5 weeks with approximate temperatures of 12° C. day/8° C. night.

*Time to produce a rooted young plant in summer.*—3 months with approximate temperatures of 20° C. day/18° C. night.

*Time to produce a rooted young plant in winter.*—3 months with approximate temperatures of 12° C. day/8° C. night.

*Root description.*—White, dense, medium thickness, fibrous.

*Rooting habit.*—Moderately branching.

Plant description:

*Type.*—Perennial. Overall shape: Flattened globular. High temperature tolerance: Tolerant to at least 40° C. Low temperature tolerance: Hardy to at least USDA Zone 6.

*Commercial crop time.*—Approximately 12 months from rooted cutting to finish in a 15 cm container.

*Growth habit and general appearance.*—Broad upright, moderately vigorous.

*Size.*—Height from soil level to top of plant plane: Approximately 24.5 cm. Width: Approximately 45.7 cm. Rate of growth: In spring, approximately 10 cm per month.

*Branching habit.*—Moderately basal branching; pinching will improve basal branching. Quantity of branches per plant: Approximately 9.

*Stem.*—Shape: Rounded. Strength: Strong. Aspect: Erect. Length to base of inflorescence: Approximately 14.2 cm. Diameter: Approximately 6.0 mm. Length of central internode: Approximately 3.7 cm. Texture: Moderately glossy, with lenticels sparsely distributed at approximately 4 per square cm. Lenticel length: Approximately 3.0 mm. Lenticel width: Approximately 0.5 mm. Lenticel color: N186C. Color of young and mature stems: 144B.

Foliage description:

*General description.*—Quantity of leaves per stem: Approximately 8. Form: Simple. Arrangement: Opposite. Durability to stress: High.

*Leaves.*—Shape: Broadly obovate to broadly elliptic. Margin: Serrate, lower one third entire. Apex: Apiculate. Base: Attenuate. Venation pattern: Pinnate. Length of mature leaf: Approximately 9.2 cm. Width of mature leaf: Approximately 6.0 cm. Texture of upper and lower surfaces: Smooth, glaborous, moderately glossy. Color of upper surface of young foliage: 143A to 144A with venation of 145B. Color of lower surface of young foliage: 144A with venation of 145C. Color of upper surface of mature foliage: Closest to 137A with venation of 145B. Color of lower surface of mature foliage: 138B with venation of 145C.

*Petiole.*—Shape: Rounded. Length: Approximately 1.7 cm. Width: Approximately 3.0 mm. Color: 145A.

Flowering description:

*Flowering habit.*—Freely flowering under outdoor growing conditions with substantially continuous blooming from early May through October.

*Lastingness of flower on the plant.*—Approximately 4 weeks.

*Flowering response time.*—Approximately 9 weeks.

Inflorescence description:

*General description.*—Type: Compound corymb with both sterile, non-sepalous florets and fertile, sepalous florets borne on the same corymb, persistent. Quantity of inflorescences per plant: Approximately 8. Fragrance: None detected. Height: Approximately 10.3 cm. Width: Approximately 15.7 cm. Quantity of opened flowers per inflorescence: Approximately 60 sterile, and approximately 18 fertile. Rate of flower opening: Approximately 50% of the flowers at any stage.

*Peduncle.*—Strength: Strong. Aspect: Approximately a 20° angle. Length: Approximately 6.2 cm. Diameter: Approximately 4.0 mm. Texture: Moderate pubescence of short, white hairs approximately 0.3 mm in length. Color: 146C.

Flower description:

*General description.*—Type: Single, rotate. Aspect: Upright to outward.

Fertile flowers:

*Bud.*—Quantity per inflorescence: Approximately 18. Shape: Globular. Length: Approximately 5.0 mm. Diameter: Approximately 5.0 mm. Color: 143B. Rate of opening from this stage: Approximately 3 days.

*Corolla.*—Depth: Approximately 5.0 mm. Diameter: Approximately 6.0 mm.

*Petals.*—Quantity: 5, occasionally a few additional petals. Appearance: Dull. Shape: Ovate, concave. Margin: Entire. Apex: Acute. Length: Approximately 4.0 mm. Width: Approximately 3.0 mm. Texture of upper and lower surfaces: Smooth. Color of upper surface when first and fully open: 143C with 144C at base. Color of lower surface when first and fully open: 143B.

*Calyx.*—Shape: Campanulate. Length: Approximately 4.0 mm. Diameter: Approximately 5.0 mm.

*Sepals.*—Quantity: 5. Arrangement: Rotate. Appearance: Dull. Shape: Ovate, lower 5 percent fused. Margin: Entire. Apex: Acute. Base: Cuneate. Length: Approximately 2.0 mm. Width: Approximately 1.5 mm. Texture of upper and lower surfaces: Smooth.

Color of upper surface of immature and mature sepals: 144B. Color of lower surface of immature and mature sepals: 144B.

*Pedicel.*—Strength: Moderate. Aspect: Approximately at a 5° angle. Length: Approximately 3.0 mm. Diameter: Approximately 1.0 mm. Texture: Smooth, glabrous. Color: 177D.

*Reproductive organs.*—Androecium: Stamen quantity: 10 per flower. Anther shape: Kidney. Anther length: Approximately 1.5 mm. Filament length: Approximately 1.5 mm. Anther color: 145C to 145D. Filament color: 145A to 145B. Pollen amount: None detected. Gynoecium: Pistil quantity: Typically 3, occasionally 2 per flower. Pistil length: Approximately 2.0 mm. Stigma shape: Club. Stigma color: 145B. Style length: Approximately 1.5 mm. Style color: 145B to 145C. Ovary color: 145B to 145C.

Sterile flowers:

*Bud.*—Quantity per inflorescence: Approximately 60. Shape: Ovate. Length: Approximately 8.0 mm. Diameter: Approximately 5.0 mm. Color: 145C. Rate of opening from this stage: Approximately 3 days.

*Corolla.*—Depth: Approximately 1.8 cm. Diameter: Approximately 4.8 cm.

*Petals.*—Quantity: 5. Appearance: Dull. Shape: Ovate, concave. Margin: Entire. Apex: Acute. Length: Approximately 4.0 mm. Width: Approximately 2.0 mm. Texture of upper and lower surfaces: Smooth. Color of upper surface when first and fully open: 143C with 144C at base. Color of lower surface when first open: 145C. Color of lower surface when fully open: 143B.

*Bracts.*—Quantity: 4, occasionally 5. Shape: Broadly deltoid to broadly elliptic. Margin: Serrate, lower one third entire. Apex: Rounded to bluntly acute. Base: Cuneate. Length: Approximately 2.4 cm. Width: Approximately 2.1 cm. Texture of upper and lower surfaces: Smooth. Color of upper surface of immature bracts: N144C marbled with 63C with venation of 145C to 145D. Color of lower surface of immature and mature bracts: 145C marbled with 63D with indistinguishable venation. Color of upper surface of mature bracts: 145A to 145B marbled with 63C with indistinguishable venation. With age bracts fade to N144D marbled with 65C to 65D.

*Pedicel.*—Strength: Moderate. Aspect: Approximately at a 50° angle. Length: Approximately 2.8 cm. Diameter: Approximately 2.0 mm. Texture: Smooth, glabrous. Color: 186D.

Seed and fruit production: Neither seed nor fruit production has been observed.

Disease and pest resistance: No particular resistance or susceptibility to diseases or insects noted to date.

What is claimed is:

1. A new and distinct cultivar of *Hydrangea* plant named 'Fantasia', substantially as herein shown and described.

* * * * *